US008809303B2

(12) United States Patent
Egan

(10) Patent No.: US 8,809,303 B2
(45) Date of Patent: Aug. 19, 2014

(54) METHODS OF REGULATING ACTIN CYTOSKELETAL REARRANGEMENT AND INTERCELLULAR GAP FORMATION

(75) Inventor: Thomas Michael Egan, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 12/936,801

(22) PCT Filed: Apr. 9, 2009

(86) PCT No.: PCT/US2009/040098
§ 371 (c)(1),
(2), (4) Date: Nov. 12, 2010

(87) PCT Pub. No.: WO2009/126822
PCT Pub. Date: Oct. 15, 2009

(65) Prior Publication Data
US 2011/0053871 A1 Mar. 3, 2011

Related U.S. Application Data

(60) Provisional application No. 61/043,586, filed on Apr. 9, 2008.

(51) Int. Cl.
A61K 31/70 (2006.01)

(52) U.S. Cl.
USPC .......................................................... 514/62

(58) Field of Classification Search
USPC .......................................................... 514/62
See application file for complete search history.

(56) References Cited

U.S. PATENT DOCUMENTS

| 5,628,984 | A | 5/1997 | Boucher, Jr. |
| 6,113,918 | A | 9/2000 | Johnson et al. |
| 6,699,846 | B2 | 3/2004 | Elliott et al. |
| 7,202,234 | B2 | 4/2007 | Chow et al. |
| 2005/0227943 | A1 | 10/2005 | Johnson et al. |
| 2006/0058365 | A1 | 3/2006 | Kohn et al. |
| 2006/0211752 | A1 | 9/2006 | Kohn et al. |
| 2012/0064044 | A1 | 3/2012 | Egan |

FOREIGN PATENT DOCUMENTS

| WO | WO97/43899 | 11/1997 |
| WO | WO98/50399 | 11/1998 |
| WO | WO01/53462 | 7/2001 |
| WO | WO01/70209 | 9/2001 |
| WO | WO03/105909 | 12/2003 |
| WO | WO2005/117975 | 12/2005 |
| WO | WO2007/107285 | 9/2007 |
| WO | WO2009/019260 | 2/2009 |
| WO | WO2009/126822 | 10/2009 |
| WO | WO2010/118334 | 10/2010 |

OTHER PUBLICATIONS

Egan et al., "A Strategy to Increase the Donor Pool: Use of Cadaver Lungs for Transplantation," Ann. Thorac. Surg. vol. 52 pp. 1113-1121 (1991).
Notification Concerning Transmittal of International Preliminary Report on Patentability (Chapter I of the Patent Cooperation Treaty) corresponding to International Application No. PCT/US2010/030556 dated Oct. 20, 2011.
Official Action corresponding to Chinese Patent Application No. 200980121482.3 dated Oct. 28, 2011.
Official Action corresponding to Israeli Patent Application No. 208565 dated Aug. 25, 2011.
Official Action corresponding to Mexican Patent Application No. MX/a/2010/011050 dated Sep. 19, 2011.
Supplementary European Search Report corresponding to European Patent Application No. 09730162.6-2123 dated Oct. 4, 2011.
Adachi et al., "Targeted Disruption of the MyD88 Gene Results in Loss of IL-1- and IL-18-Mediated Function," Immunity. vol. 9 pp. 143-150 (1998).
Casiraghi et al, "Toll-Like Receptor-4 (TLR4) Inhibition Reduces Actin Cytoskeletal Re-Arrangement and Gap Formation in Cultured Human Pulmonary Microvascular Endothelial Cells (HMVECs) Subjected to Simulated Warm Ischemia-Reperfusion Injury (IRI)," The Journal of Heart and Lung Transplantation. vol. 27, No. 2S pp. S214-S215 (2008) [Abstract].
Casiraghi et al., "Toll-like receptor-4 (TLR4) inhibition reduces actin cytoskeletal re-arrangement and gap formation in cultured human pulmonary microvascular endothelial cells (HMVECs) subjected to simulated warm ischemia-reperfusion injury (IRI)," UNC School of Medicine Presentation (Apr. 9, 2008).
Chow et al., "Toll-like Receptor-4 Mediates Lipopolysaccharide-induced Signal Transduction," The Journal of Biological Chemistry. vol. 274, No. 16 pp. 10689-10692 (1999).
Cluff et al., "Synthetic Toll-Like Receptor 4 Agonists Stimulate Innate Resistance to Infectious Challenge," Infection and Immunity. vol. 73, No. 5 pp. 3044-3052 (2005).
de Groot, H., and Rauen, U., "Ischemia-Reperfusion Injury: Processes in Pathogenetic Networks: A Review," Transplantation Proceedings. vol. 39 pp. 481-484 (2007).
de Perrot et al., "Ischemia-Reperfusion-induced Lung Injury," Am. J. Respir. Crit. Care Med. vol. 167 pp. 490-511 (2003).
Dudek, S.M., and Garcia, J.G.N., "Cytoskeletal regulation of pulmonary vascular permeability," J. Appl. Physiol. vol. 91 pp. 1487-1500 (2001).
Egan, "Non-heart-beating Donors in Thoracic Transplantation," The Journal of Heart and Lung Transplantation. vol. 23, No. 1 pp. 3-10 (2004).
Ingber, "Cellular mechanotransduction: putting all the pieces together again," The FASEB Journal. vol. 20 pp. 811-827 (2006).
Jones et al., "When does the lung die? $K_{fc}$, cell viability, and adenine nucleotide changes in the circulation-arrested rat lung," J. Appl. Physiol. vol. 83, No. 1 pp. 247-252 (1997).

(Continued)

Primary Examiner — Elli Peselev
(74) Attorney, Agent, or Firm — Jenkins, Wilson, Taylor & Hunt, P.A.

(57) ABSTRACT

Methods are described for reducing cytoskeletal rearrangement and intercellular gap formation by contacting cells with an aminoalkyl glucosaminide phosphate. In particular, the methods can be used to reduce actin cytoskeletal rearrangement and/or intracellular gap formation related to ischemic or ischemia-reperfusion events and to alleviate diseases or conditions related to increased actin cytoskeletal rearrangement.

15 Claims, 4 Drawing Sheets

(56) References Cited

OTHER PUBLICATIONS

King et al., "Reperfusion Injury Significantly Impacts Clinical Outcome After Pulmonary Transplantation," Ann. Thorac. Surg. vol. 69 pp. 1681-1685 (2000).

Koukoulis et al., "Trends in Lung pH and $pO_2$ After Circulatory Arrest: Implications for Non-Heart-Beating Donors and Cell Culture Models of Lung Ischemia-Reperfusion Injury," The Journal of Heart and Lung Transplantation. vol. 24, No. 12 pp. 2218-2225 (2005).

Lee et al., "Saturated Fatty Acids, but Not Unsaturated Fatty Acids, Induce the Expression of Cyclooxygenase-2 Mediated through Toll-like Receptor 4," The Journal of Biological Chemistry. vol. 276, No. 20 pp. 16683-16689 (2001).

Matthay et al., "Alveolar Epithelium," Proc. Am. Thorac. Soc. vol. 2 pp. 206-213 (2005).

Mollen et al., "Emerging Paradigm: Toll-Like Receptor 4—Sentinel for the Detection of Tissue Damage," Shock. vol. 26, No. 5 pp. 430-437 (2006).

Notification Concerning Transmittal of International Preliminary Report on Patentability (Chapter I of the Patent Cooperation Treaty) corresponding to International Application No. PCT/US2009/040098 dated Oct. 21, 2010.

Notification of Transmittal of the International Search Report and the Written Opinion of the International Searching Authority, or the Declaration corresponding to International Application No. PCT/US2009/040098 dated Oct. 15, 2009.

Notification of Transmittal of the International Search Report and the Written Opinion of the International Searching Authority, or the Declaration corresponding to International Application No. PCT/US2010/030556 dated Jul. 7, 2010.

Powell, C.S., and Jackson, R.M., "Mitochondrial complex I, aconitase, and succinate dehydrogenase during hypoxia-reoxygenation: modulation of enzyme activities by MnSOD," Am. J. Physiol. Lung Cell Mol. Physiol. vol. 285 pp. L189-L198 (2003).

Sanlioglu et al.,"Lipopolysaccharide Induces Rac1-dependent Reactive Oxygen Species Formation and Coordinates Tumor Necrosis Factor-α Secretion through IKK Regulation of NF-κB," The Journal of Biological Chemistry. vol. 276, No. 32 pp. 30188-30198 (2001).

Shimamoto et al., "Toll-Like Receptor 4 Mediates Lung Ischemia-Reperfusion Injury," Ann. Thorac. Surg. vol. 82, No. 6 pp. 2017-2023 (2006).

Steen et al., "First Human Transplantation of a Nonacceptable Donor Lung After Reconditioning Ex Vivo," Ann. Thorac. Surg. vol. 83 pp. 2191-2194 (2007).

Stöver et al., "Structure-Activity Relationship of Synthetic Toll-like Receptor 4 Agonists," The Journal of Biological Chemistry. vol. 279, No. 6 pp. 4440-4449 (2004).

Taylor et al., "Recognition of Hyaluronan Released in Sterile Injury Involves a Unique Receptor Complex Dependent on Toll-like Receptor 4, CD44, and MD-2," The Journal of Biological Chemistry. vol. 282, No. 25 pp. 18265-18275 (2007).

Zanotti et al., "Critical Role of Toll-like Receptor (TLR) 4 in Lung Ischemia-Reperfusion Injury (IRI)," J. Heart Lung Transplant. vol. 25, No. 2 p. S54 (2006) [Abstract].

Zanotti et al., "Novel critical role of Toll-like receptor 4 in lung ischemia-reperfusion injury and edema," Am. J. Physiol. Lung Cell Mol. Physiol. vol. 297 pp. L52-L63 (2009).

Zanotti et al., "Toll-like receptor 4 (TLR4) on lung parenchymal cells: a critical mediator of ischemia-reperfusion injury (IRI)," Proc. Am. Thorac. Soc. vol. 3 p. A685 (2006) [Abstract].

Zhang et al., "Carbon Monoxide Inhibition of Apoptosis during Ischemia-Reperfusion Lung Injury is Dependent on the p38 Mitogen-activated Protein Kinase Pathway and Involves Caspase 3," The Journal of Biological Chemistry. vol. 278, No. 2 pp. 1248-1258 (2003).

Cho, H., and Kleeberger, S.R., "Genetic mechanisms of susceptibility to oxidative lung injury in mice," Free Radical Biology & Medicine. vol. 42, No. 4 pp. 433-445 (2007).

Egan et al., "Complement-Mediated Pulmonary Edema in Sheep," Journal of Surgical Research. vol. 45, No. 2 pp. 204-214 (1988).

Egan et al., "Ex Vivo Evaluation of Human Lungs for Transplant Suitability," Ann. Thorac. Surg. vol. 81, No. 4 pp. 1205-1213 (2006).

Egan et al., "Trigger for Intercellular Adhesion Molecule-1 Expression in Rat Lungs Transplanted From Non-Heart-Beating Donors," Ann. Thorac. Surg. vol. 77, No. 3 pp. 1048-1055 (2004).

Fort et al., "A Synthetic TLR4 Antagonist Has Anti-Inflammatory Effects in Two Murine Models of Inflammatory Bowel Disease," The Journal of Immunology. vol. 174, No. 10 pp. 6416-6423 (2005).

Harari et al., "Absence of TRAM Restricts Toll-Like Receptor 4 Signaling in Vascular Endothelial Cells to the MyD88 Pathway," Circulation Research. vol. 98, No. 9 pp. 1134-1140 (2006).

Hollingsworth et al., "The Critical Role of Hematopoietic Cells in Lipopolysaccharide-induced Airway Inflammation," American Journal of Respiratory and Critical Care Medicine. vol. 171, No. 8 pp. 806-813 (2005).

Hollingsworth et al., "The Role of Toll-like Receptor 4 in Environmental Airway Injury in Mice," American Journal of Respiratory and Critical Care Medicine. vol. 170, No. 2 pp. 126-132 (2004).

Inokawa et al., "Ex-Vivo Perfusion and Ventilation of Rat Lungs From Non-Heart-Beating Donors Before Transplant," Ann. Thorac. Surg. vol. 82, No. 4 pp. 1219-1225 (2006).

Janssens, S., and Beyaert, R., "Role of Toll-like Receptors in Pathogen Recognition," Clinical Microbiology Reviews. vol. 16, No. 4 pp. 637-646 (2003).

Jiang et al., "Regulation of lung injury and repair by Toll-like receptors and hyaluronan," Nat. Med. vol. 11, No. 11 pp. 1173-1179 (2005).

Kim et al., "Ischemia-Reperfusion Injury Activates Innate Immunity in Rat Kidneys," Transplantation. vol. 79, No. 10 pp. 1370-1377 (2005).

Kleeberger et al., "Toll-like receptor 4 mediates ozone-induced murine lung hyperpermeability via inducible nitric oxide synthase," Am. J. Physiol. Lung Cell Mol. Physiol. vol. 280, No. 2 pp. L326-L333 (2001).

Naidu et al., "Early activation of the alveolar macrophage is critical to the development of lung ischemia-reperfusion injury," The Journal of Thoracic and Cardiovascular Surgery. vol. 126, No. 1 pp. 200-207 (2003).

Nürnberger et al., "Innate immunity in plants and animals: striking similarities and obvious differences," Immunological Reviews. vol. 198 pp. 249-266 (2004).

O'Neill, "TLRs play good cop, bad cop in the lung," Nature Medicine. vol. 11, No. 11 pp. 1161-1162 (2005).

O'Neill, L.A. J., and Bowie, A.G., "The family of five: TIR-domain-containing adaptors in Toll-like receptor signalling," Nature Reviews: Immunology. vol. 7, No. 5 pp. 353-364 (2007).

Oyama et al., "Reduced Myocardial Ischemia-Reperfusion Injury in Toll-Like Receptor 4-Deficient Mice," Circulation. vol. 109, No. 6 pp. 784-789 (2004).

Parker, R.E., and Brigham, K.L., "Effects of endotoxemia on pulmonary vascular resistances in unanesthetized sheep," J. Appl. Physiol. vol. 63, No. 3 pp. 1058-1062 (1987).

Saria, A., and Lundberg, J.M., "Evans blue fluorescence: quantitative and morphological evaluation of vascular permeability in animal tissues," Journal of Neuroscience Methods. vol. 8, No. 1 pp. 41-49 (1983).

Schwaller et al., "Transformation of hematopoietic cell lines to growth-factor independence and induction of a fatal myelo- and lymphoproliferative diseases in mice by retrovirally transduced *TEL/JAK2* fusion genes," The Embo Journal. vol. 17, No. 18 pp. 5321-5333 (1998).

Shimamoto et al., "Inhibition of Toll-like Receptor 4 With Eritoran Attenuates Myocardial Ischemia-Reperfusion Injury," Circulation. vol. 114, Suppl. 1 pp. I-270-I-274 (2006).

Sioud et al., "Signaling through Toll-like Receptor 7/8 Induces the Differentiation of Human Bone Marrow CD34+ Progenitor Cells along the Myeloid Lineage," J. Mol. Biol. vol. 364, No. 5 pp. 945-954 (2006).

Takashima et al., "Inhaled nitric oxide reduces ischemia-reperfusion injury in rat lungs form non-heart-beating donors," The Journal of Thoracic and Cardiovascular Surgery. vol. 132, No. 1 pp. 132-139 (2006).

(56) References Cited

OTHER PUBLICATIONS

Tsung et al, "Hepatic Ischemia/Reperfusion Injury Involves Functional TLR4 Signaling in Nonparenchymal Cells," The Journal of Immunology. vol. 175, No. 11 pp. 7661-7668 (2005).

Wierup et al., "Ex Vivo Evaluation of Nonacceptable Donor Lungs," Ann. Thorac. Surg. vol. 81, No. 2 pp. 460-466 (2006).

Wu et al., "Airway epithelial cell tolerance to *Pseudomonas aeruginosa*," Respiratory Research. vol. 6, No. 1 p. 26 (2005).

Wu et al., "TLR4 activation mediates kidney ischemia/reperfusion injury," The Journal of Clinical investigation. vol. 117, No. 10 pp. 2847-2859 (2007).

Wu et al., "Toll-like receptor 4 involvement in hepatic ischemia/reperfusion injury in mice," Hepatobiliary & Pancreatic Diseases International. vol. 3, No. 2 pp. 250-253 (2004).

Xu et al., "Structural basis for signal transduction by the Toll/interleukin-1 receptor domains," Nature. vol. 408, No. 6808 pp. 111-115 (2000).

Zhang et al., "Cutting Edge: TLR4 Deficiency Confers Susceptibility to Lethal Oxidant Lung Injury," The Journal of Immunology. vol. 175, No. 8 pp. 4834-4838 and 8439-8444 (2005).

Zhang et al., "Toll-like receptor 4 deficiency causes pulmonary emphysema," The Journal of Clinical Investigation. vol. 116, No. 11 pp. 3050-3059 (2006).

Official Action corresponding to Chinese Patent Application No. 200980121482.3 dated Aug. 7, 2012.

Official Action corresponding to Mexican Patent Application No. MX/a/2010/011050 dated Apr. 3, 2012.

Official Action corresponding to Eurasian Patent Application No. 201001450 dated Sep. 13, 2012.

Official Action corresponding to Chinese Patent Application No. 200980121482.3 dated Mar. 8, 2013.

Official Action corresponding to European Patent Application No. 09 730 162.6-2123 dated Feb. 4, 2013.

Official Action corresponding to Israeli Patent Application No. 208565 dated Dec. 16, 2012.

Official Action corresponding to Israeli Patent Application No. 215604 dated Nov. 19, 2012.

Official Action corresponding to U.S. Appl. No. 13/263,435 dated Mar. 28, 2013.

Intent to Grant corresponding to Chinese Patent Application No. 200980121482.3 dated Sep. 26, 2013.

Official Action corresponding to Japanese Patent Application No. 2011-504178 dated Oct. 3, 2013.

Chong et al., "Toll-like receptor 4 mediates ischemia/reperfusion injury of the heart," The Journal of Thoracic and Cardiovascular Surgery. vol. 128, No. 2 pp. 170-179 (2004).

Lauenstein, "MRI of inflammatory bowel disease," Applied Radiology. pp. 19-24 (2008).

Official Action corresponding to U.S. Appl. No. 13/263,435 dated Aug. 19, 2013.

Welbourn et al., "Pathophysiology of ischaemia reperfusion injury: central role of the neutrophil," British Journal of Surgery. vol. 78 pgs. 651-655 (1991).

Xiong et al., "The expression of toll-like receptor 2, 4 of livers in mice with systemic inflammatory response syndrome," Hepatobillary & Pancreatic Diseases International. vol.5, No. 1 pp. 143-146 (2006).

Okayama University's HP, "Okayama University Graduate School of Medicine, General Thoracic Surgery and Breast and Endocrinological Surgery (second surgery)," (2008).

Extended European Search Report corresponding to European Patent Application No. 10762505.5—1464 dated Feb. 25, 2014.

Issued Patent corresponding to Chinese Patent Application Serial No. 200980121482.3 dated Jan. 15, 2014.

Klausner et al., "Reperfusion Pulmonary Edema," JAMA. vol. 261, No. 7 pp. 1030-1035 (1989).

Written Opinion and Search Report corresponding to Hungarian Patent Application No. 201107347-5 dated Nov. 28, 2013.

Yang et al., "Upregulated expression of toll-like receptor 4 in monocytes correlates with severity of acute cerebral infarction," Journal of Cerebral Blood Flow & Metabolism. vol. 28, No. 9 pp. 1588-1596 (2008).

Zhai et al., "Evidence for the Pivotal Role of Endoqenous Toll-Like Receptor 4 Ligands in Liver Ischemia and Reperfusion Injury," Transplantation. vol. 85, No. 7 pp. 1016-1022 (2008).

Official Action corresponding to U.S. Appl. No. 13/263,435 dated Apr. 14, 2014.

METHODS OF REGULATING ACTIN CYTOSKELETAL REARRANGEMENT AND INTERCELLULAR GAP FORMATION

RELATED APPLICATIONS

This application claims the benefit of U.S. Patent Application Ser. No. 61/043,586, filed Apr. 9, 2008, the disclosure of which is incorporated herein by reference in its entirety.

TECHNICAL FIELD

The presently disclosed subject matter relates to methods and compositions for reducing or preventing actin cytoskeletal rearrangement and intercellular gap formation. The methods can be used to prevent actin cytoskeletal rearrangement that occurs in response to an ischemic event or an ischemia-reperfusion injury.

ABBREVIATIONS

° C.=degrees Celsius
AGP=aminoalkyl glucosaminide phosphate
ARDS=Adult Respiratory Distress Syndrome
ATP=adenosine triphosphate
CI=cold ischemia
$CO_2$=carbon dioxide
HMVECs=human pulmonary microvascular endothelial cells
hr=hours
IRI=ischemia-reperfusion injury
LDH=lactate dehydrogenase
kg=kilogram
μmol=micromole
mg=milligram
min=minutes
$O_2$=oxygen
PBS=phosphate buffered saline
SIRS=Systemic Inflammatory Response Syndrome
WI=warm ischemia

BACKGROUND

Acute lung injury is a feature of sepsis, systemic inflammatory response, and adult respiratory distress syndrome. Non-cardiogenic pulmonary edema and impaired gas exchange are consequences of acute lung injury, irrespective of etiology. The mechanisms causing pulmonary edema due to acute lung injury are not well understood. Ischemia-reperfusion injury (IRI), a form of acute lung injury occurring immediately following lung transplantation, is a frequent complication causing morbidity and mortality. See King et al., *Ann. Thorac. Surg.*, 69, 1681-1685 (2000).

Reperfusion following an interval of ischemia results in an inflammatory response involving components of the innate immune system, including the complement and coagulation cascades. Both parenchymal and myeloid cells elaborate free radicals, nitric oxide, and pro- and anti-inflammatory cytokines. See de Perrot et al., *Am. J. Respir. Crit. Care Med.*, 167(4), 490-511 (2003); de Groot and Rauen, *Transplant Proc.*, 39(2), 481-484 (2007); and Mollen et al., *Shock*, 26(5), 430-437 (2006).

A greater understanding of lung IRI is likely relevant to many types of acute lung injury, and can be of benefit to substantial numbers of patients, in addition to lung transplant recipients. Such knowledge can also potentially be used to facilitate the retrieval of lungs from non-heart-beating cadaver donors for transplant, and/or assist in the salvage of sub-transplant quality lungs, See Steen et al. *Ann Thorac Surg.*, 83, 2191-2195 (2007) thereby addressing the critical shortage of transplantable lungs. See Egan et al., *Ann. Thorac. Surg.*, 52, 1113-1121 (1991) and Egan, *J. Heart Lung Transplant.*, 23(1), 3-10 (2004).

SUMMARY

In some embodiments, the presently disclosed subject matter provides a method of preventing or reducing actin cytoskeletal rearrangement in a cell, the method comprising contacting the cell with an effective amount of a compound of Formula (I):

wherein:
n is an integer from 1 to 6;
$X_1$ is O or S;
$X_2$ is O or S;
$R_1$, $R_2$, and $R_3$ are independently $C_2$-$C_{16}$ acyl, wherein at least one of $R_1$, $R_2$, and $R_3$ is $C_2$-$C_7$ acyl;
$R_4$ is selected from the group consisting of H, hydroxyalkyl, —C(=O)$NH_2$, and —$(CH_2)_m$C(=O)OH, wherein m is an integer from 0 to 2; and
$R_5$, $R_6$, and $R_7$ are independently $C_{10}$-$C_{12}$ alkyl, or a pharmaceutically acceptable salt thereof.

In some embodiments, n is 1. In some embodiments, $X_1$ and $X_2$ are each O. In some embodiments, $R_4$ is —C(=O)OH. In some embodiments, $R_1$, $R_2$, and $R_3$ are each $C_2$-$C_7$ acyl. In some embodiments, the compound of Formula (I) is a compound wherein n is 1; $X_1$ is O; $X_2$ is O; $R_1$, $R_2$ and $R_3$ are each —C(=O)($CH_2)_4CH_3$; $R_4$ is —C(=O)OH; and $R_5$, $R_6$, and $R_7$ are each —$(CH_2)_{10}CH_3$, or a pharmaceutically acceptable salt thereof.

In some embodiments, the cell is a mammalian cell. In some embodiments, the cell is an endothelial cell.

In some embodiments, preventing or reducing actin cytoskeletal rearrangement prevents or reduces intercellular gap formation between the cell and one or more cells surrounding the cell.

In some embodiments, contacting the cell occurs prior to an ischemic or ischemia-reperfusion-related event, during ischemia, or after an interval of ischemia, and preventing or reducing actin cytoskeletal rearrangement comprises preventing or reducing actin cytoskeletal rearrangement related to an ischemic or ischemia-reperfusion-related event.

In some embodiments, the presently disclosed subject matter provides a method of preventing or reducing actin cytoskeletal rearrangement in one or more cells in a subject, the method comprising administering to the subject an effective amount of a compound of Formula (I) or a pharmaceutically acceptable salt thereof.

In some embodiments, preventing or reducing actin cytoskeletal rearrangement in one or more cells in the subject prevents or alleviates a disease or condition associated with increased actin cytoskeletal rearrangement, or a symptom thereof, in the subject. In some embodiments, the subject is a mammal.

It is an object of the presently disclosed subject matter to provide methods and compositions for preventing or reducing actin cycloskeletal rearrangement.

An object of the presently disclosed subject matter having been stated hereinabove, and which is achieved in whole or in part by the presently disclosed subject matter, other objects will become evident as the description proceeds when taken in connection with the accompanying examples and drawings as best described hereinbelow.

DETAILED DESCRIPTION

Figure 1A:
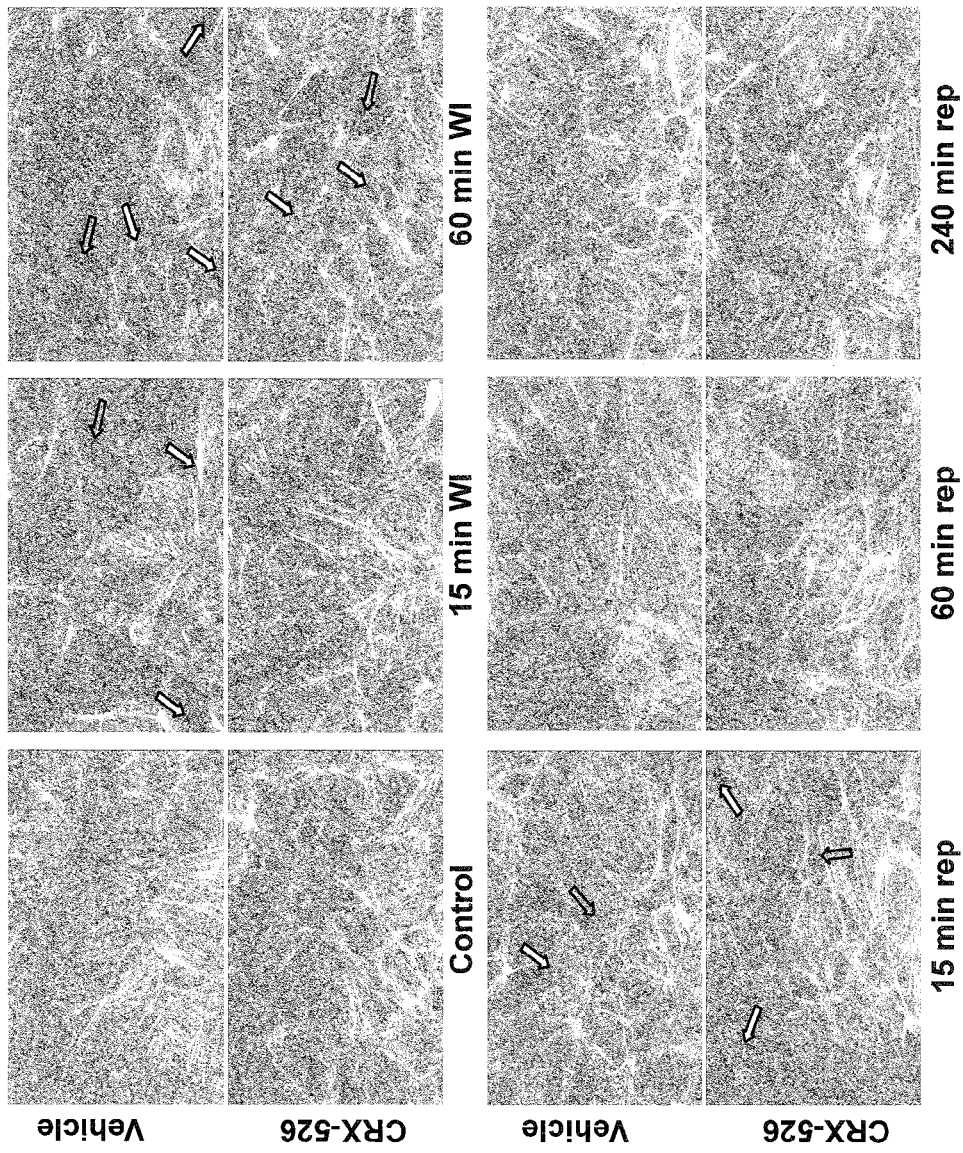
FIG. 1A is a series of photographs of phallodian stained human pulmonary microvascular endothelial cells (HM-VECs) showing the effect of simulated warm ischemia without hypoxia on actin cytockeletal rearrangement and on the formation of gaps in the human pulmonary microvascular endothelial monolayer. The HMVECs were grown to confluence on P30 dishes with integral cover slips and incubated with either 1 µg/mL CRX-526 or vehicle prior to 1 hour of simulated warm ischemia (WI). The photographs show CRX-526-treated and vehicle-treated cells prior to WI (Control), after 15 or 60 min WI, and after 15, 60, or 240 min of simulated reperfusion (rep). Experiments were performed in triplicate.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a compound" or "a cell" includes a plurality of such compounds or cells, and so forth.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tent-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 6 carbon atoms (i.e., a $C_{1-7}$ alkyl), e.g., 1, 2, 3, 4, 5, or 6 carbon atoms. "Higher alkyl" refers to an alkyl group having about 8 to about 20 carbon atoms, e.g., 8, 9, 10, 11, 12, 13, 14, 15, 16, 17, 18, 19, or 20 carbon atoms.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "alkenyl" refers to an alkyl group comprising one or more carbon-carbon double bonds.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

"Hydroxy" and "hydroxyl" refer to the group —OH.

The term "hydroxyalkyl" refers to a hydroxy-terminated alkyl group. In some embodiments, the hydroxyalkyl group has the structure —$(CH_2)_n$OH.

The term "carboxylic acid" refers to the group —C(=O)OH. The term "carboxylate" refers to anion formed when the H of the carboxylic acid group is removed. Thus, "carboxylate" refers to the group —C(=O)O$^-$. Carboxylates can form salts (i.e., carboxylate salts) with cationic groups. The terms "alkylene carboxylate" and "alkylene carboxylic acid" refer to monovalent groups formed by the attachment of a carboxylic acid or carboxylate group to one open attachment point on an alkylene group (e.g., the groups —$(CH_2)_n$C(=O)OH and —$(CH_2)_n$C(=O)O$^-$).

As used herein, the term "acyl" refers to the group —C(=O)R, wherein R is an alkyl or aryl group as defined hereinabove. In some embodiments, the R of the acyl group is $C_1$-$C_{16}$ alkyl. In some embodiments, the alkyl group of the acyl moiety is straight chain alkyl or alkenyl. In some embodiments the R of the acyl group is $C_1$-$C_{16}$ straight chain alkyl.

The term "phosphate" refers to the group —P(=O)(OH)$_2$. The term "phosphate" also includes anionic species formed by the removal of one or more hydrogen atoms of the phosphate group.

The term "thiol" refers to a group having the structure —S—R, wherein R is alkyl, acyl, or aryl. The term "thiol" can also refer to a compound having the structure H—S—R, wherein R is alkyl, acyl, or aryl.

The term "amino" refers to a group having the structure —$NR_1R_2$, wherein $R_1$ and $R_2$ are independently selected from the group H, alkyl, acyl, and aryl.

The term "carbamoyl" refers to the group —C(=O)NH$_2$.

The term "monosaccharide" refers to a carbohydrate monomer unit of the formula $(CH_2O)_{n+m}$ based upon an open chain form of a compound having the chemical structure H(CHOH)$_n$C(=O)(CHOH)$_m$H, wherein the sum of n+m is an integer between 2 and 8. Thus, the monomer units can include trioses, tetroses, pentoses, hexoses, heptoses, nonoses, and mixtures thereof. The monosaccharide can be in a cyclized form of the chemical structure. Thus, in some embodiments, the compound will comprise a hemiacetal or hemiketal. In some embodiments, the term "monosaccharide" refers to a cyclized monomer unit based on a compound having a chemical structure H(CHOH)$_n$C(=O)(CHOH)$_m$H wherein n+m is 4 or 5. Thus, monosaccharides include, but are not limited to, aldohexoses, aldopentoses, ketohexoses, and ketopentoses such as arabinose, lyxose, ribose, xylose, ribulose, xylulose, allose, altrose, galactose, glucose, gulose, idose, mannose, talose, fructose, psicose, sorbose, and tagatose.

The term "monosaccharide analog" refers to a monosaccharide wherein one or more hydroxyl group of the monosaccharide is replaced by another chemical group, such as, but not limited to a phosphate, an amine, a thiol, or an alkyl group.

The term "amino sugar" refers to a monosaccharide analog wherein one or more hydroxyl group of a monosaccharide is replaced by an amine. An exemplary amino sugar is glucosamine (i.e., 2-deoxy-2-amino-α-D-glucopyranose).

The term "fragment" as used herein with relation to a compound, refers to a compound whose structure is any portion of the structure of the originally named compound that is less than the whole of the originally named compound. Thus, a fragment is smaller than the original compound, but generally retains some or all of the biological activity of the original compound.

"Pharmaceutically acceptable" refers to those compounds, materials, compositions, and/or dosage forms that are, within the scope of sound medical judgment, suitable for contact with the tissues of human beings and animals without excessive toxicity, irritation, allergic response, or other problems or complications commensurate with a reasonable benefit/risk ratio. Thus, in some embodiments, the presently disclosed compounds, materials, compositions, and/or dosage forms are pharmaceutically acceptable for use in humans.

Generally, the term "reducing" refers to methods of treating a pre-existing condition or disease by, for example, reducing or alleviating the symptoms or effects of the condition or disease, to any degree.

"Preventing" refers to methods of keeping a potential future condition, disease, disorder, or injury, or the symptoms thereof, from occurring, to any degree. "Preventing" can refer to methods of decreasing the effects of a future condition or injury, such that the effects of the future condition or injury are of lesser magnitude or shorter duration than the effects that would have occurred in the absence of the preventative action, as well as to methods of completely keeping the effects from occurring. Thus, "preventing" refers to prophylactic methods of medical and veterinary treatment.

"Ischemia" refers to inadequate blood flow to a biological tissue or organ, which results in the organ or tissue's inability to meet demands for metabolism. Reperfusion (resumption of blood flow) to the ischemic organ or tissue can lead to the production of excessive amounts of reactive oxygen species (ROS) and reactive nitrogen species (RNS), thus causing oxidative stress which results in a series of events such as alterations in mitochondrial oxidative phosphorylation, depletion of ATP (which also occurs during and as a result of ischemia), an increase in intracellular calcium and activation of protein kinases, phosphatases, proteases, lipases and nucleases leading to loss of cellular function/integrity.

Ischemia reperfusion injury (IRI) refers to an injury which occurs after blood circulation is restarted in an organic tissue subjected to ischemia (e.g., when an organ is excised by operation and re-attached, as in a transplant or auto-transplant). By way of additional example and not limitation, such injury also occurs when blood circulation is restarted after being stopped for the transplantation of an organ; after a coronary artery is treated with percutaneous transluminal coronary angioplasty (PTCA), stent, or bypass after myocardial infarction; and after administration of a thrombolytic to a stroke patient. Another example is when blood flow to the heart is temporarily stopped for cardiac surgery, often by the prior administration of cardioplegia solutions. Another example is interruption of blood flow to a limb for surgery in a bloodless field by an orthopedic surgeon when a tourniquet is inflated on the limb. Such an injury can occur in many tissues, such as kidney, liver, lungs, pancreas, skeletal muscle, smooth muscle soft tissue, skin, and intestines, as well as in the heart and brain. Thus, IRI can include, but is not limited to, cerebral, retinal, hepatic, renal, pancreatic, spinal cord, mesenteric, limb, intestinal, brain, myocardial, central nervous system, skin, or lung ischemia reperfusion injury, or a combination thereof. In particular, ischemia-reperfusion injury is a serious problem in organ transplantation because the harvested organ is removed from the body of a donor, isolated from a blood source, and thus deprived of nutrients and often oxygen for an extended period of time, typically.

"Edema" refers to an increase in interstitial fluid in a tissue or organ. In the lung, "edema" can also refer to an increase in alveolar fluid. In some embodiments, edema is associated with a condition involving increased endothelial cell permeability.

"Increased endothelial permeability" refers to increased permeability of blood vessels in an organ or tissue to fluid and/or protein in the blood, resulting in edema, which can occur in a number of clinical scenarios, such as, but not limited to, Adult Respiratory Distress Syndrome (ARDS), Systemic Inflammatory Response Syndrome (SIRS) and in the setting of infection with a variety of bacteria.

II. General Considerations

The endothelial cytoskeleton, particularly actin stress fibers, plays a role in regulation of pulmonary vascular permeability. See Dudek and Garcia, *J. Appl. Physiol.,* 91(4), 1487-1500 (2001). It has also been postulated that the cytoskeleton can function as an intracellular communication system or signaling scaffold. See Ingber, *Faseb J.,* 20(7), 811-827, (2006). The presently disclosed subject matter relates to the observation that an aminoalkyl glucosaminide phosphate, CRX-526, reduces cytoskeletal rearrangement following simulated ischemia.

III. Lipid A Mimetics

In some embodiments, the presently disclosed subject matter relates to the use of lipid A mimetic compounds that comprise monosaccharides or monosaccharide analogs. In some embodiments, the monosaccharide analog is an amino sugar. In some embodiments, the amino sugar is glucosamine. In some embodiments, the presently disclosed subject matter relates to the use of aminoalkyl glucosaminide phosphates (AGPs) or pharmaceutically acceptable salts thereof.

III.A. Compounds of Formula (I)

In general, AGPs are synthetic (i.e., chemically synthesized) lipid A mimetics and can have a structure of Formula (I):

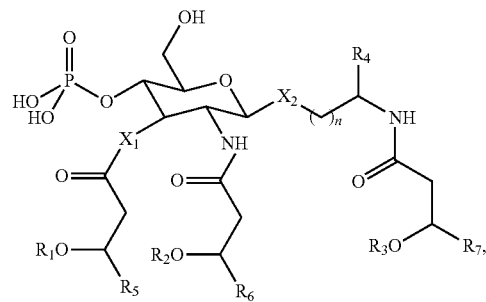

wherein:
  n is an integer from 1 to 6;
  $X_1$ is O or S;
  $X_2$ is O or S;
  $R_1$, $R_2$, and $R_3$ are independently $C_2$-$C_{16}$ acyl;
  $R_4$ is selected from the group consisting of H, hydroxylalkyl, —C(=O)NH$_2$, and —(CH$_2$)$_m$C(=O)OH, wherein m is an integer from 0 to 2; and
  $R_5$, $R_6$, and $R_7$ are independently $C_{10}$-$C_{12}$ alkyl, or a pharmaceutically acceptable salt thereof.

Generally, the AGP for use in the presently disclosed subject matter include at least one secondary acyl chain (i.e., $R_1$, $R_2$, or $R_3$) that is less than eight carbons. Thus, in some embodiments, at least one of $R_1$, $R_2$ and $R_3$ is —C(=O)$R_8$, wherein $R_8$ is $C_1$-$C_6$ alkyl (i.e., at least one of $R_1$, $R_2$, and $R_3$ is $C_2$-$C_7$ acyl). In some embodiments, at least two of $R_1$, $R_2$, and $R_3$ are $C_2$-$C_7$ acyl. In some embodiments, at least one of $R_1$, $R_2$ and $R_3$ is —C(=O)$R_8$, wherein $R_8$ is $C_5$ alkyl. In some embodiments, $R_5$, $R_6$, and $R_7$ are each $C_{10}$-$C_{12}$ straight-chain, fully saturated alkyl.

In some embodiments, the compound is CRX-526, i.e., the compound of Formula (I) wherein n is 1; $X_1$ and $X_2$ are each O; $R_1$, $R_2$ and $R_3$ are each —C(=O)(CH$_2$)$_4$CH$_3$; $R_4$ is —C(=O)OH; and $R_5$, $R_6$, and $R_7$ are each —(CH$_2$)$_{10}$CH$_3$, or a pharmaceutically acceptable salt thereof.

The synthesis and activity of a variety of AGPs have been previously described. See, e.g., Cluff et al., *Infection and Immunity*, 73(5), 3044-3052 (2005); Stöver et al., *J. Biol. Chem.*, 279(6), 4440-4449 (2004); and references cited therein. See also, U.S. Pat. No. 6,113,918 to Johnson et al.

The compounds of Formula (I) have asymmetric carbon atoms and can therefore exist as enantiomers or diastereomers. Diasteromeric mixtures can be separated into their individual diastereomers on the basis of their physical chemical differences by methods known per se, for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of the presently disclosed subject matter.

III.B. Pharmaceutically Acceptable Salts

The expression "pharmaceutically acceptable salt" as used herein in relation to compounds of the presently disclosed subject matter (e.g., the compounds of Formula (I)) includes pharmaceutically acceptable cationic salts. The expression "pharmaceutically-acceptable cationic salts" is intended to define but is not limited to such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, ethanolamine, diethanolamine, triethanolamine, ethylenediamine, meglumine (N-methylglucamine), benethamine (N-benzylphenethylamine), ethanolamine, diethylamine, piperazine, triethanolamine (2-amino-2-hydroxymethyl-1,3-propanediol) and procaine. In some embodiments, the term "pharmaceutically acceptable salt" as used herein refers to salts that are pharmaceutically acceptable in humans.

Pharmaceutically acceptable salts of the compounds of Formula (I) can be readily prepared by reacting the free acid form of said compounds with an appropriate base, usually one or more equivalent, in a co-solvent. Co-solvents can include, but are not limited to, diethylether, diglyme and acetone. Bases can include, but are not limited to, sodium hydroxide, sodium methoxide, sodium ethoxide, sodium hydride, potassium methoxide, magnesium hydroxide, calcium hydroxide, benzathine, choline, ethanolamine, diethanolamine, piperazine and triethanolamine. The salt is isolated by concentration to dryness or by addition of a non-solvent. In many cases, salts can be prepared by mixing a solution of the acid with a solution of a different salt of the cation (e.g., sodium or potassium ethylhexanoate, magnesium oleate) and employing a co-solvent, as described above, from which the desired cationic salt precipitates, or can be otherwise isolated by concentration.

IV. Methods of Preventing or Reducing Actin Cytoskeletal Rearrangement in a Cell In some embodiments, the presently disclosed subject matter relates to methods of preventing or reducing actin cytoskeletal rearrangement. In some embodiments, the presently disclosed subject matter provides a method of preventing or reducing actin cytoskeletal rearrangement in a cell, the method comprising contacting the cell with an effective amount of a compound of Formula (I):

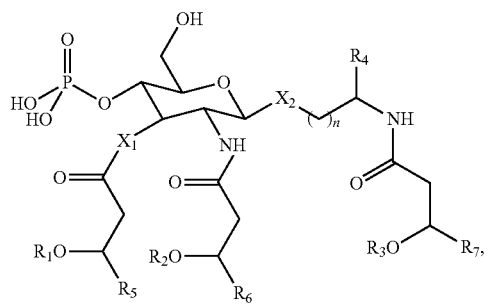

wherein:
n is an integer from 1 to 6;
$X_1$ is O or S;
$X_2$ is O or S;
$R_1$, $R_2$, and $R_3$ are independently $C_2$-$C_{16}$ acyl;
$R_4$ is selected from the group consisting of H, hydroxylalkyl, —C(=O)NH$_2$, and —(CH$_2$)$_m$C(=O)OH, wherein m is an integer from 0 to 2; and
$R_5$, $R_6$, and $R_7$ are independently $C_{10}$-$C_{12}$ alkyl, or a pharmaceutically acceptable salt thereof.

In some embodiments, at least one of $R_1$, $R_2$ and $R_3$ is —C(=O)$R_8$, wherein $R_8$ is $C_5$ straight-chain, fully saturated alkyl. In some embodiments, $R_5$, $R_6$, and $R_7$ are each $C_{10}$-$C_{12}$ straight-chain, fully saturated alkyl.

In some embodiments, n is 1. In some embodiments, $X_1$ and $X_2$ are each O. In some embodiments, $R_4$ is —C(=O) OH. In some embodiments, $R_1$, $R_2$, and $R_3$ are each $C_2$-$C_7$ acyl.

In some embodiments, the compound is CRX-526, i.e., the compound of Formula (I) wherein n is 1; $X_1$ and $X_2$ are each O; $R_1$, $R_2$ and $R_3$ are each —C(=O)(CH$_2$)$_4$—CH$_3$; $R_4$ is —C(=O)OH; and $R_5$, $R_6$, and $R_7$ are each —(CH$_2$)$_{10}$CH$_3$, or a pharmaceutically acceptable salt thereof.

The cell of the presently disclosed methods can be any suitable cell. Suitable cells include, but are not limited to, osteoblasts, osteoclasts, chondrocytes, adipocytes, fibroblasts, endothelial cells, epithelial cells, mesenchymal cells, hematopoietic cells, sensory cells, endocrine and exocrine glandular cells, glia cells, neuronal cells, oligodendrocytes, blood cells, intestinal cells, brain cells, cardiac cells, lung cells, liver cells, kidney cells, muscle cells, and pancreatic cells. In some embodiments, the cell is a eukaryotic cell. In some embodiments, the cell is a mammalian cell. In some embodiments, the cell is a human cell.

In some embodiments, the cell is an endothelial cell. In some embodiments, the presently disclosed subject matter relates to regulation of endothelial cell permeability. Thus, in some embodiments, the presently disclosed subject matter provides a method of regulating endothelial cell permeability, wherein the method comprises contacting an endothelial cell with a compound of Formula (I). Regulation of cell permeability can result in the maintenance of normal levels of interstitial fluid (and/or alveolar fluid) surrounding the contacted cell or in a decrease in interstitial fluid (and/or alveolar fluid). In some embodiments, regulation of cell permeability prevents an increase in interstitial fluid or alveolar fluid that would otherwise have resulted from a disease or event (such as infection or an ischemia-reperfusion injury).

In some embodiments, the method of preventing or reducing actin cytoskeletal rearrangement prevents or reduces intercellular gap formation between the cell and one or more additional cells surrounding the cell. The actin cytoskeletal rearrangement can be associated with edema, including pulmonary edema or edema in other organs. The edema can be associated with inflammation, infection, trauma (e.g., surgery), inhalation of a toxin, a circulatory disorder, or exposure to high altitudes. In some embodiments, preventing or reducing actin cytoskeletal rearrangement comprises preventing or reducing actin cytoskeletal rearrangement that is associated with a condition characterized by increased endothelial permeability.

In some embodiments, the edema to be prevented or reduced is associated with ischemia-reperfusion, such as during organ transplantation, pulmonary embolectomy (removal of clotted blood from pulmonary arteries), or pulmonary thromboendarterectomy (surgical removal of organized clot and fibrin from the pulmonary vasculature).

In some embodiments, the cell is contacted with an effective amount of the compound of Formula (I) prior to a simulated or predicted ischemic or ischemia-reperfusion event (e.g., removal of tissue for organ transplant, tissue transplant, cardioplegia, application of a tourniquet, etc.) to prevent or reduce actin cytoskeletal rearrangement during the ischemia or subsequent reperfusion. In some embodiments, the cell can be contacted with the compound of Formula (I) during ischemia. In some embodiments, the cell can be contacted with the compound of Formula (I) after an interval of ischemia (e.g., during reperfusion).

In some embodiments, the ischemia-reperfusion event is related to myocardial infarction or stroke. In some embodiments, the ischemia-reperfusion event is related to cardioplegia (i.e., when cardiac activity is stopped intentionally) during cardiac surgery or to ischemia in skeletal muscle resulting from orthopedic surgery (e.g., when a tourniquet is applied to a limb to reduce blood in the surgical field).

In some embodiments, the presently disclosed subject matter relates to in vitro or ex vivo methods, wherein the cell is not located in a living organism.

For example, the cell can be present in a cell culture or in an ex vivo tissue or organ. In some embodiments, such in vitro or ex vivo methods can be used to determine the relative ability of compounds to prevent or reduce actin cytoskeletal rearrangement or to determine a dosage of a particular compound in a particular cell type. In some embodiments, an ex vivo method can be used to treat a cell present in a tissue or organ intended for transplant.

V. Methods of Preventing or Reducing Actin Cytoskeletal Rearrangement in a Subject In some embodiments, the cell is present in a living organism. Thus, in some embodiments, the presently disclosed subject matter provides a method of preventing or reducing actin cytoskeletal rearrangement in one or more cells in a subject, the method comprising administering to the subject an effective amount of a compound of Formula (I):

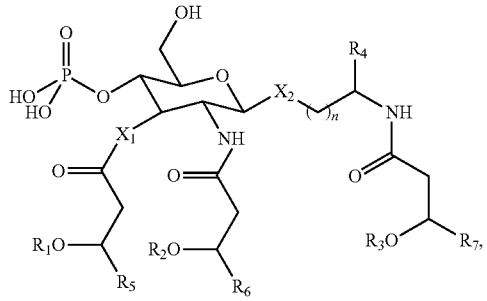

wherein:
n is an integer from 1 to 6;
$X_1$ is O or S;
$X_2$ is O or S;
$R_1$, $R_2$, and $R_3$ are independently $C_2$-$C_{16}$ acyl;

$R_4$ is selected from the group consisting of H, hydroxylalkyl, —C(=O)NH$_2$, and —(CH$_2$)$_m$C(=O)OH, wherein m is an integer from 0 to 2; and $R_5$, $R_6$, and $R_7$ are independently $C_{10}$-$C_{12}$ alkyl, or a pharmaceutically acceptable salt thereof.

In some embodiments, at least one of $R_1$, $R_2$ and $R_3$ is —C(=O)R$_8$, wherein $R_8$ is $C_5$ straight-chain, fully saturated alkyl. In some embodiments, $R_5$, $R_6$, and $R_7$ are each $C_{10}$-$C_{12}$ straight-chain, fully saturated alkyl.

In some embodiments, n is 1. In some embodiments, $X_1$ and $X_2$ are each O. In some embodiments, $R_4$ is —C(=O)OH. In some embodiments, $R_1$, $R_2$, and $R_3$ are each $C_2$-$C_7$ acyl.

In some embodiments, the compound is CRX-526, i.e., the compound of Formula (I) wherein n is 1; $X_1$ and $X_2$ are each O; $R_1$, $R_2$ and $R_3$ are each —C(=O)(CH$_2$)$_4$—CH$_3$; $R_4$ is —C(=O)OH; and $R_5$, $R_6$, and $R_7$ are each —(CH$_2$)$_{10}$CH$_3$, or a pharmaceutically acceptable salt thereof.

In some embodiments, preventing or reducing actin cytoskeletal rearrangement in one or more cells in the subject prevents or alleviates a disease or condition associated with increased actin cytoskeletal rearrangement, or a symptom thereof, in the subject. The disease or condition can be any disease or condition characterized by edema. In some embodiments, the edema is associated with increased epithelial cell permeability. For example, the disease or condition is ARDS or SIRS.

In some embodiments, the disease or condition is associated with IRI. Accordingly, the disease or condition can be related to IRI associated with organ or tissue transplantation (including xeno-transplantation or auto-transplantation), cardioplegia, myocardial infarction, stroke, elective orthopedic surgery, liver surgeries involving the Pringle maneuver, or other surgeries wherein blood flow is restricted to a tissue. In some embodiments, the condition can be related to IRI associated with lung transplant.

The administration of the compound of Formula (I) can be via any suitable route (i.e., oral, intravenous, parenteral, via the airway, etc.). The contacting can take place prior to an ischemic event, during ischemia, or following an interval is ischemia (e.g., during reperfusion).

In some embodiments, the subject is a mammal. In some embodiments, the subject is a human. In some embodiments, the cell or cells are present in an organ or tissue selected from the group including, but not limited to, a kidney or a portion thereof, a liver or a portion thereof, a heart or a portion thereof, a retina, a pancreas or a portion thereof, a bowel or a portion thereof, brain tissue, skeletal muscle, or a lung or a portion thereof.

VI. Pharmaceutical Compositions

As used herein, the term "active compound" refers to any compound that can inhibit cytoskeletal rearrangement and/or intercellular gap formation. In particular, the term refers to compounds of Formula (I) and their salts. The active compound can be contacted to the cell or administered to the subject through any suitable approach. As used herein, the term "effective amount" refers to an amount of active compound or active compounds which is capable of inhibiting or preventing various pathological conditions and sequelae, herein described. The terms "inhibit" or "inhibiting" refers to prohibiting, preventing, treating, alleviating, ameliorating, halting, restraining, reducing, slowing or reversing the progression, or reducing the severity of a pathological condition, such as, but not limited to, a condition related to or resultant from tissue damage (e.g., lung tissue damage) in subjects who are at risk for diseases or conditions related to increased cytoskeletal rearrangement. As such, the presently disclosed methods of administering active compounds include both medical therapeutic (acute) and/or prophylactic (prevention) administration, as appropriate.

The amount and timing of active compound administered can, of course, be dependent on the subject being treated, on the severity of the affliction, on the manner of administration and on the judgment of the prescribing physician.

Thus, because of subject to subject variability, the dosages given below are a guideline and the physician can titrate doses of the compound to achieve the treatment that the physician considers appropriate for the subject. In considering the degree of treatment desired, the physician can balance a variety of factors such as age of the subject, presence of preexisting disease, as well as presence of other diseases. Pharmaceutical formulations can be prepared for oral, intravenous, or aerosol administration as discussed in greater detail below.

The therapeutically effective dosage of any specific active compound, the use of which is within the scope of embodiments described herein, can vary somewhat from compound to compound, and subject to subject, and can depend upon the condition of the subject and the route of delivery. As a general proposition, a dosage from about 0.1 to about 50 mg/kg can have therapeutic efficacy, with all weights being calculated based upon the weight of the active compound, including the cases where a salt is employed. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. In some embodiments, dosages can be from about 1 µmol/kg to about 50 µmol/kg, or, optionally, between about 22 µmol/kg and about 33 µmol/kg of the compound for intravenous or oral administration.

The in vitro and in vivo assays described herein provide an approach wherein the activities of compounds can be compared. The results of these comparisons are useful for determining dosage levels in mammals, including humans, for inducing protection from actin cytoskeletal rearrangement. Such assays provide for the comparison of activities of the compounds of Formula I and other compounds. The results of these comparisons are useful for determining such dosage levels.

In accordance with the presently disclosed methods, pharmaceutically active compounds as described herein can be administered orally as a solid or as a liquid, or can be administered intramuscularly, intravenously or via the airway (e.g., by inhalation) as a solution, suspension, or emulsion. In some embodiments, the compounds or salts also can be administered by inhalation, intravenously, or intramuscularly as a liposomal suspension. When administered through inhalation the active compound or salt can be in the form of a plurality of solid particles or droplets having a particle size from about 0.5 to about 5 microns, and optionally from about 1 to about 2 microns.

The pharmaceutical formulations can comprise an active compound described herein or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized.

In addition to the active compounds or their salts (e.g., the compounds of Formula (I)), the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules. Materials in this connection also include lactose or milk sugar as well as high molecular weight polyethylene glycols. When aqueous suspensions and/or elixirs are desired for oral administration, the compounds of the presently disclosed subject matter can be combined with various sweetening agents, flavoring agents, coloring agents, emulsifying agents and/or suspending agents, as well as such diluents as water, ethanol, propylene glycol, glycerin and various like combinations thereof.

In yet another embodiment of the subject matter described herein, there is provided an injectable, stable, sterile formulation comprising an active compound as described herein, or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. When the compound or salt is substantially water-insoluble, a sufficient amount of emulsifying agent, which is physiologically acceptable, can be employed in sufficient quantity to emulsify the compound or salt in an aqueous carrier. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, and optionally from about 0.5 to about 5 microns. The solid particles can be obtained by processing the solid compound or a salt thereof, in any appropriate manner known in the art, such as by micronization. Optionally, the size of the solid particles or droplets can be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation can comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable whereas in other embodiments water-insoluble compounds or salts likewise can be desirable.

In one mode of administration, the compounds of the presently disclosed subject matter can be administered just prior to a surgery (e.g., within twenty-four hours before surgery, for example, cardiac surgery or transplant surgery), during and/or subsequent to surgery (e.g., within twenty-four hours after surgery) where there is risk of ischemia. In another mode of administration, the active compounds are administered with an initial loading dose (e.g., bolus injection or infusion) prior to surgery followed by a constant infusion prior to, during and post surgery. The active compounds can also be administered in a chronic daily mode.

Methods of preparing various pharmaceutical compositions and with a certain amount of active ingredient are known, or can be determined, in light of this disclosure, by those skilled in this art. For examples of methods of preparing pharmaceutical compositions, see Remington's Pharmaceutical Sciences, Mack Publishing Company, Easter, Pa., 16th Edition (1980). Pharmaceutical compositions according to the presently disclosed subject matter can contain, for example, 0.0001%-95% of the active compound(s). In any event, the composition or formulation to be administered can contain a quantity of an active compound(s) in an amount effective to treat the disease/condition of the subject being treated.

In some embodiments, the methods of the presently disclosed subject matter can be used to prevent or reduce actin cytoskeletal rearrangement and/or intercellular gap formation in extracorporeal tissue or organs or in tissue or organs that are being transplanted from a tissue or organ donor into a transplant recipient. Extracorporeal tissue or organs are tissue or organs not in an individual (also termed ex vivo). For tissue and organ transplantation, donor tissue and organs removed are also susceptible to reperfusion injury during harvesting, while in transit and following transplantation into a recipient. The presently disclosed methods can be used to increase the viability of a transplantable tissue or organ by, for example, supplementing solutions used to maintain or preserve transplantable tissues or organs. For example, the methods and compositions can be used to bathe the transplantable tissue or organ during transport or can be placed in contact with the transplantable tissue or organ prior to, during or after transplantation. In some embodiments, formulations of the presently disclosed subject matter can be contacted to a tissue or organ while the tissue or organ is present in the donor.

Solutions of the presently disclosed subject matter can be used in perfusion devices (e.g., ex vivo perfusion circuits). A perfusion device as used herein is any mechanical device that be used to infuse a specific organ or the systemic circulation with a solution comprising a compound or composition. Such a device can contain one or more reservoirs. The device can include a tube, catheter, or cannula leading from the reservoir that can be inserted into an organ, vein or artery. The device can be an electromechanical device having electric pumps and devices for controlling the temperature, rate or volume of delivery of the solution. In certain embodiments, the device is programmable so that the one or more solutions are delivered in an appropriate temperature, rate or volume for a particular clinical situation, weight of the organ, or size of the organ (e.g., cardiopulmonary bypass surgery vs. kidney transplant vs. liver transplant).

VII. Subjects

In some embodiments, the subject treated in the presently disclosed subject matter is desirably a human subject, although it is to be understood the methods described herein are effective with respect to all vertebrate species, which are intended to be included in the term "subject." The methods described herein are particularly useful in the treatment and/or prevention of actin cytoskeletal rearrangement in cells of warm-blooded vertebrates. Thus, the methods can be used as treatment for mammals and birds. In some embodiments, the subject of the presently disclosed method is an organ transplant recipient.

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided herein is the treatment of birds, including the treatment of those kinds of birds that are endangered, kept in zoos or as pets, as well as fowl, and more particularly domesticated fowl, i.e., poultry, such as turkeys, chickens, ducks, geese, guinea fowl, and the like, as they also are of economical importance to humans. Thus, embodiments of the methods described herein include the treatment of livestock, including, but not limited to, domesticated swine (pigs and hogs), ruminants, horses, poultry, and the like.

EXAMPLES

The following Examples provide illustrative embodiments. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

General Methods

Cell Culture Model of Warm Lung IRI

An in vitro normothermic (37° C.) model of IRI employing nutrient depletion in 100% oxygen to model ischemia was developed, with reperfusion modeled by supplying fresh medium to culture dishes in sealed PLEXIGLAS® containers. Human pulmonary microvascular endothelial cells (HMVECs) (Cambrex Bio Science, Walkersville, Md., United States of America) maintained in CLONETICS® EGM-2MV BULLETKITS® (Cambrex Bio Science, Walkersville, Md., United States of America), at 37° C. in a humidified incubator in 5% $CO_2$ were seeded at 2000 cells/cm$^2$ on collagen-coated 30 mm diameter glass bottom dish coverslips (Mattek Corp., Ashland, Mass., United States of America) and grown until 100% confluent. Sealed PLEXIGLAS® containers housing culture dishes at 37° C. were ventilated with 95% $O_2$/5% $CO_2$. To model warm ischemia (WI), cell medium was suddenly replaced with 2 mL nutrient-depleted, pyrogen-free clinical grade Ringer's lactate. Dishes were pre-treated with 1 µg/mL CRX-526 (GlaxoSmithKline, Duluth, Minn., United States of America) or vehicle (2% glycerin), one hour before WI. CRX-526 or vehicle was added whenever medium was changed. After 1 hour of simulated WI, Ringer's lactate was replaced with EGM2-MV pyrogen-free medium to simulate reperfusion, ventilating the chamber with 5% $CO_2$ in room air. Dishes were removed in triplicate during WI and reperfusion, and immediately fixed in 4% paraformaldehyde for phalloidin staining. Cells with inhibitor or vehicle maintained in EGM2-MV medium at 37° C. in humidified 5% $CO_2$ incubator served as controls. Culture medium was changed at the same time that medium was changed in experimental dishes. Probes inserted through sealed ports continuously recorded temperature, and pH in a representative dish in the PLEXIGLAS® box using voltmeters with data output recorded by PicoRecorded software (Pico Technology, St. Neots, United Kingdom).

Phalloidin Staining and Image Analysis

HMVECs were fixed in 4% paraformaldehyde for 10 minutes at room temperature and washed 3 times with PBS. Cells were incubated for 1 hour with a 1/100 dilution of ALEXA-FLOR® 568 phalloidin (Invitrogen, Carlsbad, Calif., United States of America) in PBS with 1% BSA and 0.05% Tween-20. Coverslips stained for F-actin were immediately examined with a Leica DMIRB Inverted Fluorescence/DIC microscope (Leica Microsystems, Inc., Bannockburn, Ill., United States of America) at 20× and 40× magnification to evaluate changes in cell shape and F-actin cytoskeleton. For each dish, three pictures were taken of contiguous fields near the center of the dish at 40× with a Kodak (Rochester, N.Y., United States of America) digital camera at the same exposure time. A masked observer assessed actin stress fiber pattern of each cell as normal or abnormal. Quantitative analysis of gap area was performed using METAMORPH® software (MDS Analytical Technologies, Inc., Sunnyvale, Calif., United States of America).

Determination of Viability for Cell Culture Experiments

In separate experiments performed in triplicate, HMVECs grown to confluence on P35 dishes underwent simulated IRI. At the same time points, cells and cell culture media or Ringer's lactate were assessed for lactate dehydrogenase (LDH) activity using the CytoTox96 Non-Radioactive Cytotoxicity Assay (Promega, Madison, Wis., United States of America) following the manufacturer's instructions. Control samples were also taken at time zero and 24 hours to assess cell viability apart from the experimental model. Culture medium and Ringer's lactate were used as background controls to normalize the absorbance value from the other samples. Cytotoxicity was calculated as media LDH activity divided by total LDH activity (cell pellet plus media). Viability was the inverse and expressed as percent viability at each time point.

Statistical Analysis

All data are reported as mean±SEM. Groups were compared by ANOVA with Tukey's post hoc test using STATISTICA® (StatSoft, Inc., Tulsa, Okla., United States of America) or by paired or unpaired t tests.

Example 2

Simulated Warm Ischemia-Related Actin Cytoskeletal Rearrangement and Formation of Gaps in the Endothelial Monolayer Prevented by CRX-526

An in vitro model of ischemia was used to explore inhibition of cytoskeletal rearrangement, focusing on pulmonary microvascular endothelial cells. Previous ischemia-related studies demonstrated significantly increased filtration co-efficient and W/D of rat lungs after one hour of ischemia, which was attributed to endothelial dysfunction (see Jones et al., *J. Appl. Physiol.* 83, 247-252 (1997), although altered lung epithelial fluid clearance can also contribute to pulmonary edema. See Matthay et al., *Proc. Am. Thorac. Soc.*, 2(3), 206-213 (2005). Other previous studies have employed hypoxia-reoxygenation in cell culture models of IRI. See Powell and Jackson, *Am. J. Physiol. Lung Cell Mol. Physiol.*, 285(1), L189-198 (2003); and Zhang, et al., *J. Biol. Chem.*, 278(2), 1248-1258 (2003). However, lung acidosis to pH 6.8 has been observed in rat lungs left in situ at 37° C. for 1 hour after cardiac arrest with no significant hypoxia. See Koukoulis et al., *J. Heart Lung Transplant*, 24(12), 2218-2225 (2005). Thus, hypoxia does not appear to be a general feature of lung ischemia, particularly in lungs inflated with 100% oxygen. Therefore, the presently disclosed in vitro model is believed to accurately reflect in vivo events, although nutrient depletion and development of acidosis would be more gradual in vivo.

As described in Example 1, HMVECs grown to confluence on P30 dishes with integral cover slips were incubated with 1 µg/mL CRX-526 or vehicle, ventilated with 95% $O_2$/5% $CO_2$. Media was replaced with warm (37° C.)

Ringer's lactate and ventilated with 100% $O_2$ to simulate warm ischemia. One hour later, Ringer's lactate was replaced with warm cell culture media, and chambers were ventilated with 95% room air/5% $CO_2$ to simulate reperfusion. During simulated warm ischemia, actin stress fibers disappeared or became more peripheral in the cells (see shaded arrows in FIG. 1A), associated with formation of gaps in the endothelial monolayer (see white arrows in FIG. 1A). Four hours after simulated reperfusion (240 min rep) and 24 hours after simulated reperfusion (not shown), monolayers were confluent and actin cytoskeleton pattern was similar to controls.

Figure 1B:
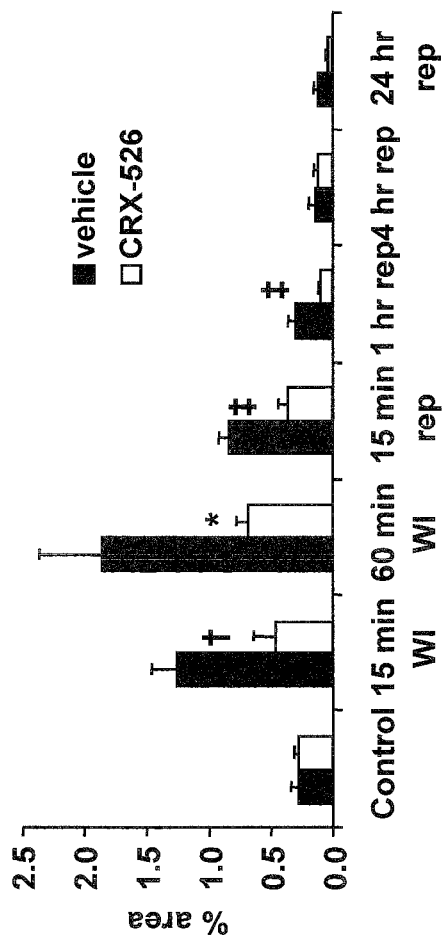
FIG. 1B is a graph of the % area of gaps in the monolayer of the cells shown in FIG. 1A. Three separate fields from each of three P30 dishes were analyzed (n=9 photos/time point). The % area of gaps in the monolayer was quantified by MetaMorph® software (MDS Analytical Technologies, Inc., Sunnyvale, Calif., United States of America). Vehicle treated cell data is shown in the shaded bars. CRX-526-treated cell data is shown in the open bars. *=$p<0.05$, †=$p<0.01$, ‡=$p<0.001$ unpaired t test.
Figure 1C:
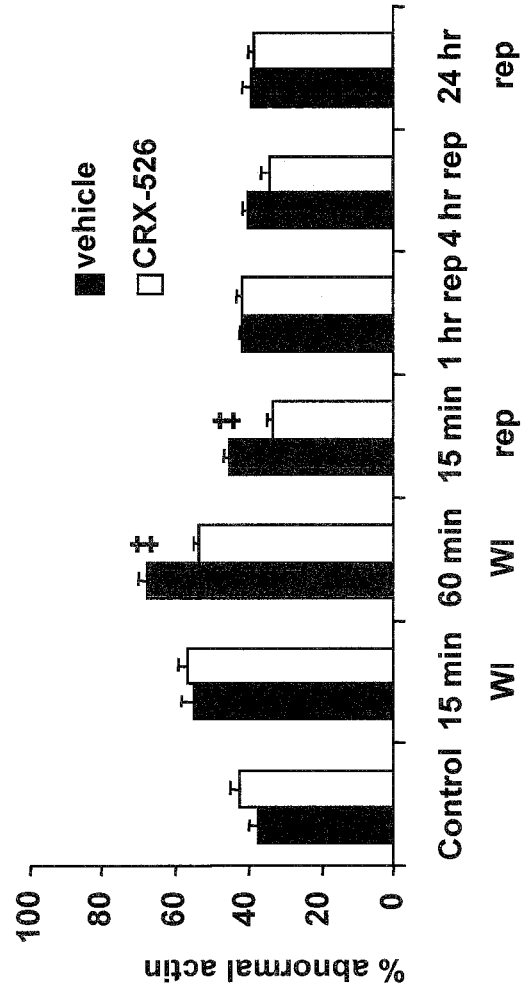
FIG. 1C is a graph of the % of abnormal actin in the cells shown in FIG. 1A. Because of considerable variability in the actin cytoskeleton of human pulmonary microvascular endothelial cells (HMVECs), cells were labeled as having "normal" or "abnormal" actin distribution in images (n=9 photos/time point), without attempting to grade the severity of the abnormality. The assessment was made by a masked observer unaware of the group identity or the time of the sample. Then, ratios of populations were calculated. Vehicle treated cell data is shown in the shaded bars. CRX-526-treated cell data is shown in the open bars. ‡=$p<0.001$ unpaired t test.

In the presence of CRX-526, the area of monolayer gaps was significantly reduced during ischemia and monolayers regained confluence more quickly after simulated reperfusion. See FIG. 1B. The percentage of cells with altered actin cytoskeleton was also decreased in monolayers by CRX-526. As indicated in FIG. 1C, approximately 40% of cells have some degree of peripheral orientation of the actin cytoskeleton in fresh control dishes. Peripheral orientation of actin was significantly reduced in the presence of CRX-526 following 60 minutes of WI and after 15 minutes simulated reperfusion (rep) compared to monolayers exposed to vehicle. Cell viability, quantified by LDH assay, was equivalent in controls and treated groups at all time points.

Replacement of medium with Ringer's lactate results in a sudden drop in pH from 7.2 to 6.5, which reverses when medium is replaced. To address whether gap formation in endothelial cell monolayers was due to changes in pH alone, experiments were performed in which the pH of cell culture medium was altered for one hour, either by ventilation of the chamber with 10% $CO_2$ (pH 6.8) or by the addition of HCl to reduce pH of the medium to 6.5 when ventilated with 100% $O_2$ or 5.6 when ventilated with 5% $CO_2$. Altered medium was replaced with normal medium to abruptly restore pH after one hour. No changes in the integrity of the monolayer were apparent when pH alone was altered.

Example 3

Simulated Cold IRI

Figure 2A:
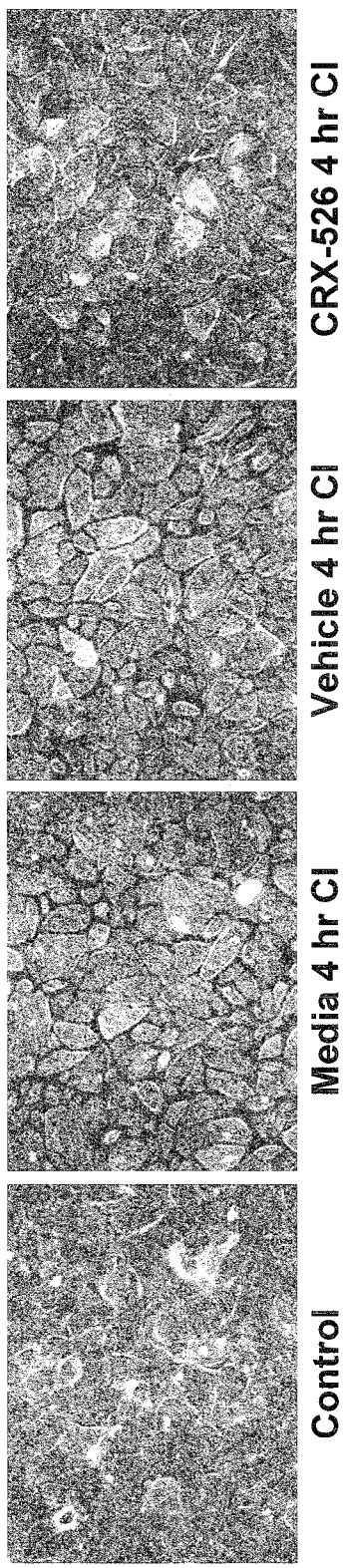
FIG. 2A is a series of photographs of (from left to right) human pulmonary microvascular endothelial cells (HM-VECs) in warm (37° C.) cell culture media (Control), of HMVECs after four hours of cold ischemia (CI) in 4° C. cell culture media (Media 4 hr CI), of HMVECs after four hours of cold ischemia in 4° C. PERFADEX™ (Vitrolife, Kungsbacka, Sweden) pulmonary preservation solution (Vehicle 4 hr CI), and of HMVECs that had been pre-incubated with CRX-526 and undergone four hours of cold ischemia in 4° C. PERFADEX™ (Vitrolife, Kungsbacka, Sweden) with CRX-526 (CRX-526 4 hr CI). The photographs are representative of 9 images taken for each set of conditions.
Figure 2B:
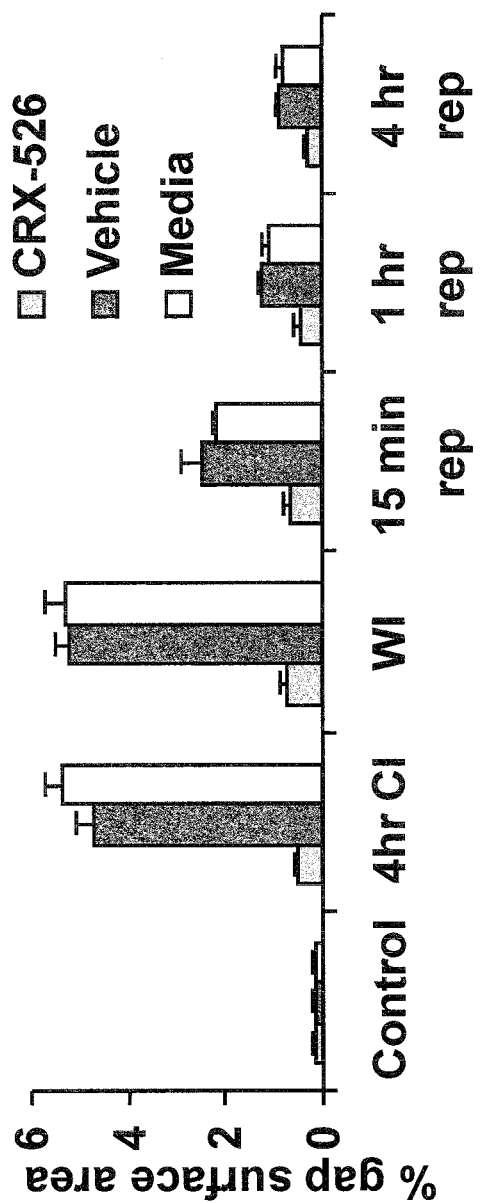
FIG. 2B is a graph of the % area of gaps in the monolayer of human pulmonary microvascular endothelial cells (HM-VECs) in cell culture media (Media), vehicle (i.e., PERFADEX™ (Vitrolife, Kungsbacka, Sweden)) or in vehicle after a 1 hour pre-treatment with CRX-526 and following either four hours of cold ischemia (4 hr CI), 1 hour of warm ischemia (WI), or following 1 hour of warm ischemia and 15 min, 1 hr, or 4 hr of reperfusion (15 min rep, 1 hr rep, and 4 hr rep, respectively). Data for the HMVECs in cell culture media without vehicle is shown in the open bars. Data for the HMVECs in media supplemented with vehicle but no compound is shown in the darkly shaded bars. Data for the CRX-526 pre-treated cells is shown in the lightly shaded bars. The % gap area was quantified by MetaMorph® software (MDS Analytical Technologies, Inc., Sunnyvale, Calif., United States of America). *=$p<0.01$.

In view of the striking impact of CRX-526 on actin cytoskeletal re-arrangement and gap formation in HMVECs subjected to simulated warm IRI, described above in Example 2, the effects of CRX-526 were also studied in a simulated model of cold IRI. FIG. 2A shows the effect of replacement of warm cell culture media with cold PERFADEX™ (Vitrolife, Kungsbacka, Sweden), the most commonly employed lung preservation solution in the world, on HMVECs. It takes about one hour for cell culture dishes to reach a temperature of 4° C., so, in FIG. 2A, photographs of cells after 4 hours of cold "ischemia" (CI) represent the appearance of cells five hours after replacement of warm media with cold PERFADEX™ (Vitrolife, Kungsbacka, Sweden) or media. Although actin cytoskeleton is deranged in all dishes, gaps are much less obvious in CRX-526-treated cells. See FIG. 2B.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of reducing actin cytoskeletal rearrangement or intercellular gap formation in a cell, the method comprising contacting the cell during cold ischemia with an effective amount of a compound of Formula (I):

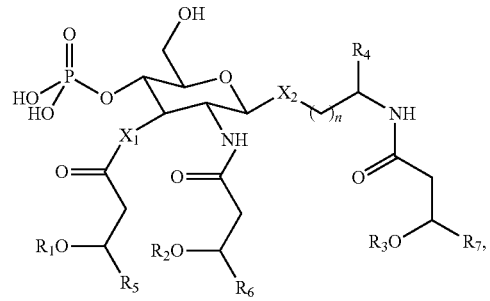

wherein:
n is an integer from 1 to 6;
$X_1$ is O or S;
$X_2$ is O or S;
$R_1$, $R_2$, and $R_3$ are independently $C_2$-$C_{16}$ acyl, wherein at least one of $R_1$, $R_2$, and $R_3$ is $C_2$-$C_7$ acyl;
$R_4$ is selected from the group consisting of H, hydroxylalkyl, —C(=O)$NH_2$, and —$(CH_2)_m$C(=O)OH, wherein m is an integer from 0 to 2; and
$R_5$, $R_6$, and $R_7$ are independently $C_{10}$-$C_{12}$ alkyl, or
a pharmaceutically acceptable salt thereof; wherein reducing actin cytoskeletal rearrangement or intercellular gap formation comprises reducing actin cytoskeletal rearrangement or intercellular gap formation during reperfusion subsequent to the cold ischemia.

2. The method of claim 1, wherein n is 1.
3. The method of claim 1, wherein $X_1$ and $X_2$ are each O.
4. The method of claim 1, wherein $R_4$ is —C(=O)OH.
5. The method of claim 1, wherein $R_1$, $R_2$, and $R_3$ are each $C_2$-$C_7$ acyl.
6. The method of claim 1, wherein the compound of Formula (I) is a compound wherein:
n is 1;
$X_1$ is O;
$X_2$ is O;
$R_1$, $R_2$ and $R_3$ are each —C(=O)$(CH_2)_4$$CH_3$;
$R_4$ is —C(=O)OH; and
$R_5$, $R_6$, and $R_7$ are each —$(CH_2)_{10}$$CH_3$, or
a pharmaceutically acceptable salt thereof.

7. The method of claim 1, wherein the cell is a mammalian cell.
8. The method of claim 7, wherein the cell is an endothelial cell.
9. The method of claim 1, wherein contacting the cell occurs during cold ischemia in a cell in an extracorporeal tissue or organ or in a tissue or organ that is being transplanted from a tissue or organ donor into a transplant recipient, and reducing actin cytoskeletal rearrangement or intercellular gap formation comprises reducing actin cytoskeletal rearrangement or intercellular gap formation related to organ or tissue transplant.
10. A method of maintaining or preserving a transplantable extracorporeal tissue or organ by reducing actin cytoskeletal rearrangement and/or intercellular gap formation in one or more cells in the tissue or organ, the method comprising contacting the transplantable extracorporeal tissue or organ during cold ischemia with a supplementing solution comprising an effective amount of a compound of Formula (I):

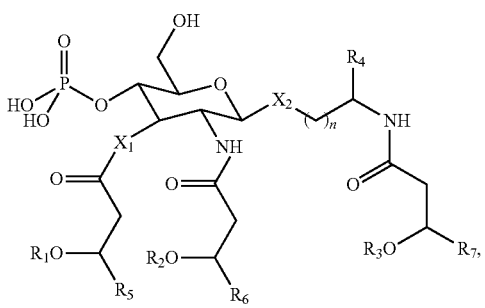

wherein:
n is an integer from 1 to 6;
$X_1$ is O or S;
$X_2$ is O or S;
$R_1$, $R_2$, and $R_3$ are independently $C_2$-$C_{16}$ acyl, wherein at least one of $R_1$, $R_2$, and $R_3$ is $C_2$-$C_7$ acyl;
$R_4$ is selected from the group consisting of H, hydroxylalkyl, —C(=O)$NH_2$, and —$(CH_2)_m$C(=O)OH, wherein m is an integer from 0 to 2; and
$R_5$, $R_6$, and $R_7$ are independently $C_{10}$-$C_{12}$ alkyl, or a pharmaceutically acceptable salt thereof, wherein reducing actin cytoskeletal rearrangement and/or intercellular gap formation in one or more cells in the tissue or organ relates to reducing actin cytoskeletal rearrangement and/or intercellular gap formation related to reperfusion injury.

11. The method of claim 10, wherein n is 1.
12. The method of claim 10, wherein $X_1$ and $X_2$ are each O.
13. The method of claim 10, wherein $R_4$ is —C(=O)OH.
14. The method of claim 10, wherein $R_1$, $R_2$, and $R_3$ are each $C_2$-$C_7$ acyl.
15. The method of claim 10, wherein the compound of Formula (I) is a compound wherein:
n is 1;
$X_1$ is O;
$X_2$ is O;
$R_1$, $R_2$ and $R_3$ are each —C(=O)$(CH_2)_4CH_3$;
$R_4$ is —C(=O)OH; and
$R_5$, $R_6$, and $R_7$ are each —$(CH_2)_{10}CH_3$, or
a pharmaceutically acceptable salt thereof.

* * * * *